(12) United States Patent
Rogers et al.

(10) Patent No.: US 12,196,763 B2
(45) Date of Patent: Jan. 14, 2025

(54) COMPOSITIONS AND METHODS FOR PREDICTING POST-SURGICAL CARDIOVASCULAR EVENTS

(71) Applicants: American Heart Association, Inc., Dallas, TX (US); Trustees of the University of Pennsylvania, Philadelphia, PA (US)

(72) Inventors: Wade T. Rogers, Philadelphia, PA (US); Jana M. Schmierer, Philadelphia, PA (US); Jonni S. Moore, Philadelphia, PA (US); Emile R. Mohler, III, Philadelphia, PA (US)

(73) Assignees: THE TRUSTEES OF THE UNIVERSITY OF PENNSYLVANIA, Pennsylvania, PA (US); AMERICAN HEART ASSOCIATION, INC, Dallas, TX (US)

( * ) Notice: Subject to any disclaimer, the term of this patent is extended or adjusted under 35 U.S.C. 154(b) by 1109 days.

(21) Appl. No.: 16/622,499

(22) PCT Filed: Jun. 13, 2018

(86) PCT No.: PCT/US2018/037338
§ 371 (c)(1),
(2) Date: Dec. 13, 2019

(87) PCT Pub. No.: WO2018/231986
PCT Pub. Date: Dec. 20, 2018

(65) Prior Publication Data
US 2021/0148931 A1    May 20, 2021

Related U.S. Application Data

(60) Provisional application No. 62/518,864, filed on Jun. 13, 2017.

(51) Int. Cl.
*G01N 31/00* (2006.01)
*G01N 33/53* (2006.01)
*G01N 33/68* (2006.01)

(52) U.S. Cl.
CPC ............... *G01N 33/6893* (2013.01); *G01N 2333/70503* (2013.01); *G01N 2333/70535* (2013.01); *G01N 2333/70557* (2013.01); *G01N 2333/70596* (2013.01); *G01N 2800/50* (2013.01); *G01N 2800/52* (2013.01)

(58) Field of Classification Search
None
See application file for complete search history.

(56) References Cited

PUBLICATIONS

Rogers et al. Vascular Health Profile Predicts Cardiovascular Outcomes in Patients with Diabetes. Cytometry Part B2017; 92B: 258-265. First Published Nov. 13, 2015. (Year: 2015).*
Mizus et al. (Arteriosclerosis, Thrombosis, and Vascular Biology. 2016;36:A355) date May 2016. (Year: 2016).*
Mizus et al. Arteriosclerosis, Thrombosis, and Vascular Biology 2016; vol. 36 No. Supp 1:Abstrcat 355 (Year: 2016).*

* cited by examiner

*Primary Examiner* — Lisa V Cook
(74) *Attorney, Agent, or Firm* — Mark S. Cohen; PEARL COHEN ZEDEK LATZER BARATZ LLP

(57) ABSTRACT

This disclosure provides for compositions and methods that can be used to predict an individual's risk for experiencing a cardiovascular event following a surgical procedure (e.g., a non-cardiac surgical procedure).

15 Claims, 3 Drawing Sheets

COMPOSITIONS AND METHODS FOR PREDICTING POST-SURGICAL CARDIOVASCULAR EVENTS

CROSS-REFERENCE

This application claims the benefit of priority to International Application No. PCT/US2018/037338, filed Jun. 13, 2018, which claims priority to U.S. Provisional Patent Application Ser. No. 62/518,864, filed Jun. 13, 2017, all of which are incorporated by reference herein in their entirety.

TECHNICAL FIELD

This disclosure generally relates to compositions and methods for predicting post-surgical cardiovascular events.

BACKGROUND

An estimated 234 million surgical cases occur worldwide each year. The impact of this burden on individual patients and society-at-large is difficult to estimate. Data suggest that in developed nations, surgical mortality may be between 0.4% and 0.8%, and complications may occur in between 3% and 17% of patients. All-cause mortality within one year after most types of surgery is higher than mortality in age- and sex-matched normal populations, reflected as increased standardized mortality ratio. This increase in mortality is more frequent in patients who are high resource consumers while in the hospital (and, therefore, likely to have had a complicated postoperative course). These data highlight peri-operative morbidity and mortality as a major public health issue.

As a result, identification of high-risk surgical patients and development of strategies aimed at reducing peri-operative morbidity and mortality is a major challenge for physicians responsible for surgery-related health care. Various interventions aimed at improving surgical outcomes have produced conflicting results in clinical trials. The development of an improved method to pre-surgically identify patients at risk of peri- or post-surgical adverse outcomes could provide valuable information for improved health care decision-making, ultimately reducing the incidence of post-surgical morbidity and mortality with concommitant decrease in cost of treatment, increases in hospital quality scores and patient quality of life.

SUMMARY

Compositions and methods are provided herein that can be used to predict an individual's risk for experiencing a cardiovascular event following a surgical procedure (e.g., a non-cardiac surgical procedure).

In one aspect, a method of predicting a cardiovascular event after a non-cardiac surgical procedure in an individual is provided. Such a method typically includes providing a biological sample from the individual; determining the number of extracellular vesicles (EVs) in the biological sample expressing a set of biological markers, the set of biological markers comprising at least one of CD31+, CD105+, or CD64+; and classifying the individual as low risk of having a post-surgical cardiovascular event or as high risk of having a post-surgical cardiovascular event based upon the number of EVs in the biological sample expressing the set of biological markers.

Representative cardiovascular events include, without limitation, myocardial infarction, emergency cardiac revascularization, stroke, death (collectively, MACE), and myocardial injury following non-cardiac surgery (MINS). Representative non-cardiac surgical procedures include, without limitation, vascular surgical procedures.

In some embodiments, the biological sample is blood. In some embodiments, determining the number of EVs utilizes high-sensitivity flow cytometry. In some embodiments, the determining step includes utilizing high-sensitivity flow cytometry.

In some embodiments, the set of biological markers includes at least two of CD31+, CD105+, or CD64+. In some embodiments, the set of biological markers comprises all three of CD31+, CD105+, or CD64+. In some embodiments, the set of biological markers includes CD31+ and CD105+. In some embodiments, the set of biological markers includes CD31+ and CD64+. In some embodiments, the set of biological markers includes CD31+, CD105+ and CD64+. In some embodiments, the set of biological markers includes CD41a−. In some embodiments, the set of biological markers comprises CD47−. In some embodiments, the set of biological markers comprises CD31+, CD105+, CD64+, CD41a− and CD47−.

In some embodiments, the method further includes preparing platelet-poor plasma (PPP) from the biological sample prior to determining the number of EVs. In some embodiments, the method further includes comparing the number of EVs in the biological sample expressing the set of biological markers to a pre-determined value, wherein the individual is classified into the low-risk group when the number of EVs in the biological sample expressing the set of biological markers is less than the pre-determined value and wherein the individual is classified into the high-risk group when the number of EVs in the biological sample expressing the set of biological markers is greater than the pre determined value.

In some embodiments, the method further includes determining the Revised Cardiac Risk Index (RCRI) for the individual. For example, the RCRI is determined using risk factors such as history of myocardial infarction, history of congestive heart failure, history of cerebrovascular disease, insulin use, and a serum creatine level of ≥2.0 ng/mL. In some embodiments, the classifying step is further based upon the Revised Cardiac Risk Index (RCRI) for the individual. In some embodiments, the classifying step is further based on combining the RCRI risk factors with the number of EVs in the biological sample.

In another aspect, a method of detecting the presence of vulnerable plaques in an individual is provided. Such a method typically includes providing a biological sample from the individual; and determining the number of monocyte-derived extracellular vesicles (MEVs) in the biological sample expressing a set of biological markers, the set of biological markers comprising at least one of CD31+, CD105+, and/or CD64+. Generally, an increase in the number of MEVs in the biological sample is indicative of plaque vulnerability.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limit-

DETAILED DESCRIPTION

Figure 1:
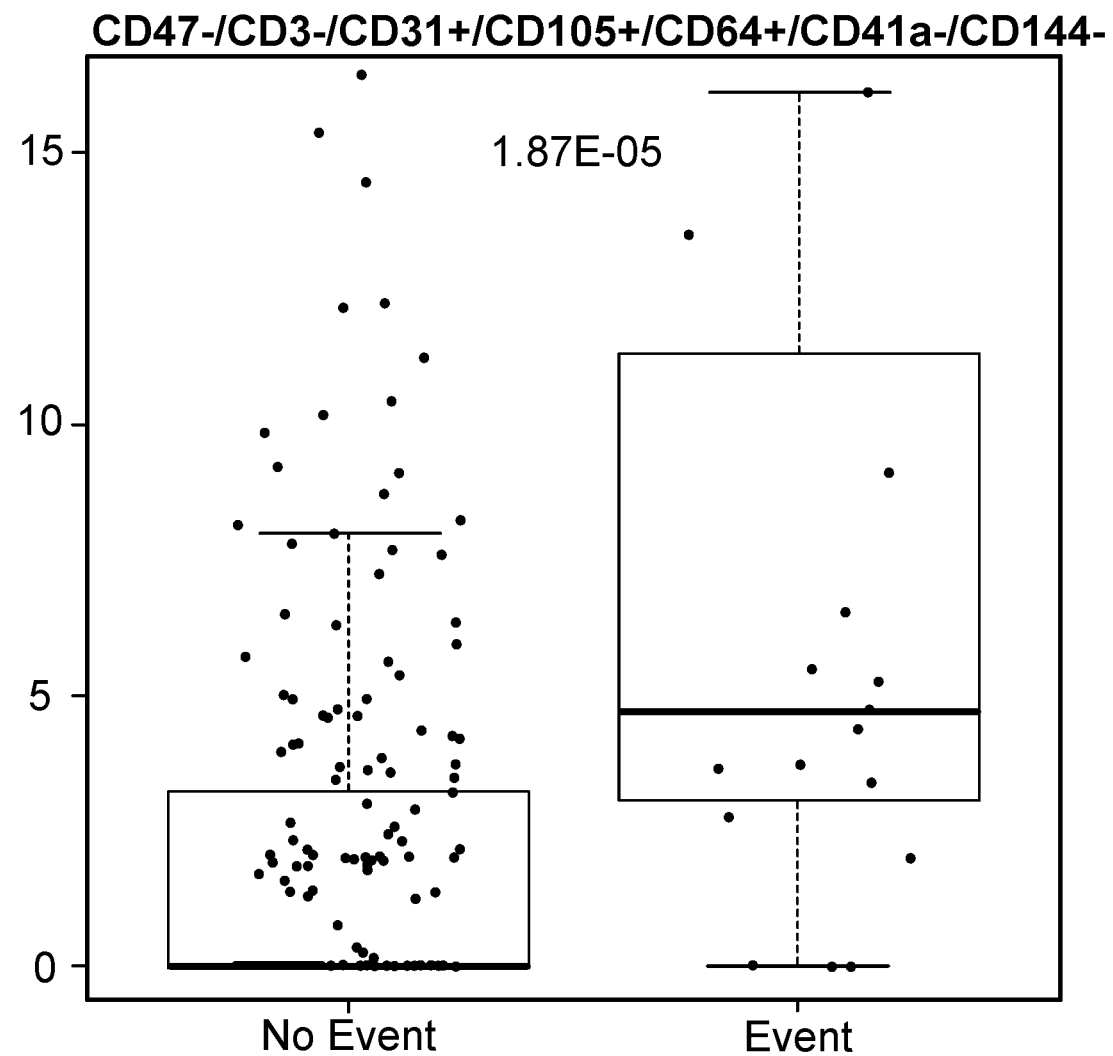
FIG. 1 is a graph comparing the discovered EV phenotype in the two groups of patients. Heavy line corresponds to the median value within-group. Box boundaries are the $1^{st}$ and $3^{rd}$ quantiles. Each dot corresponds to an individual patient. They axis has units of "EVs per µl Plasma".
Figure 2:
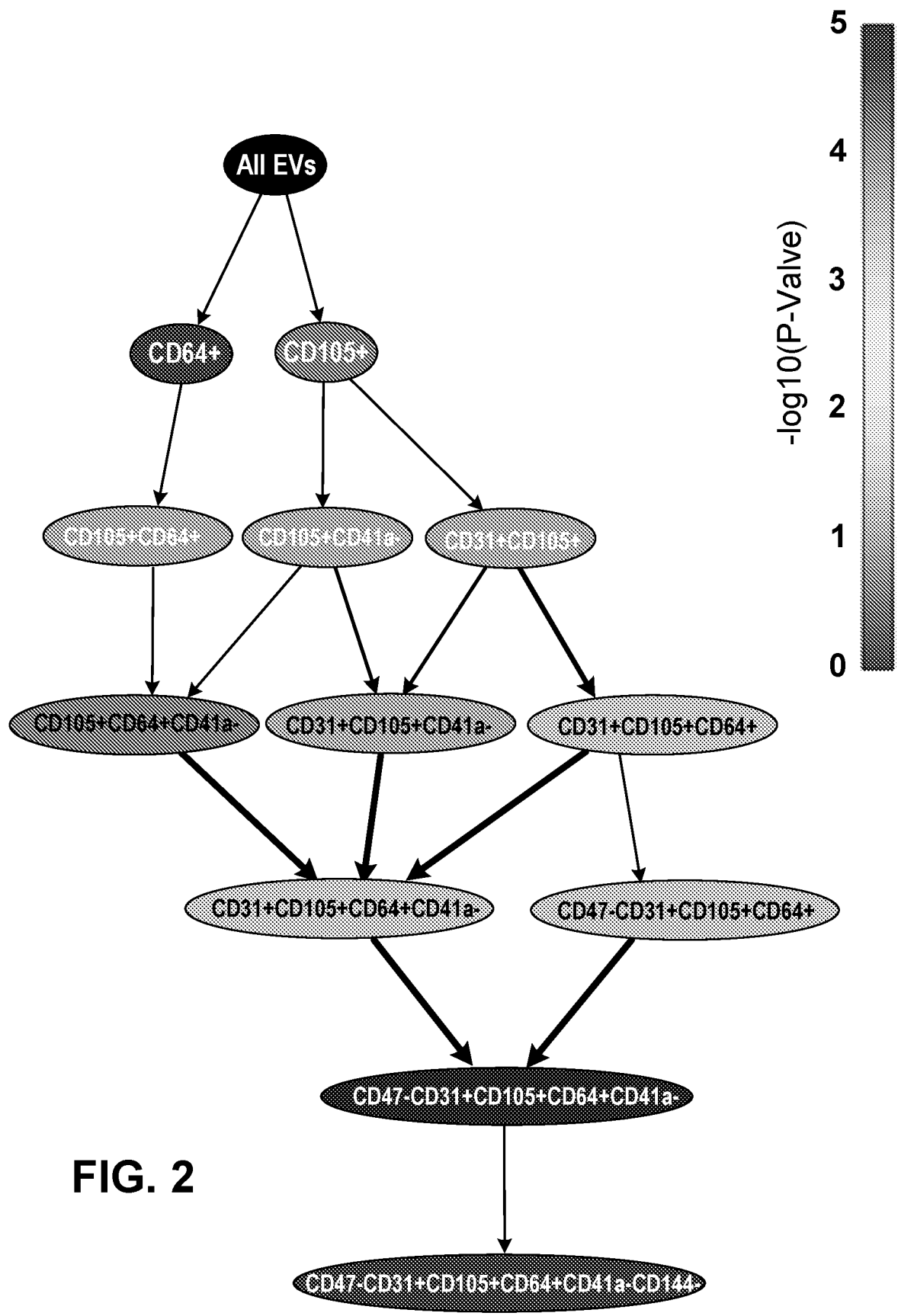
FIG. 2 is a graph showing the RchyOptimyx phenotype sensitivity analysis. The directed acyclic graph shows the evolution of statistical significance (P-value, or simply "P") with the addition of phenotypic specificity. The color scale represents $-\log_{10}(P)$, with green values denoting little significance and red denoting high significance.

The present disclosure provides a novel method of estimating or predicting the risk that an individual will experience cardiovascular complications, or a "cardiovascular event," after a non-cardiac (e.g., a vascular) surgical procedure. While the methods described herein are not specific to any particular cardiovascular event, representative cardiovascular events include, without limitation, myocardial infarction, emergency cardiac revascularization, stroke, death (collectively, MACE), and myocardial injury following non-cardiac surgery (MINS).

The current standard-of-care method of risk assessment that is widely used in hospitals in the United States is the Revised Cardiac Risk Index (RCRI)[5-13]. The RCRI is a simple scoring system that assigns one point each for (a) high-risk procedure, (b) history of myocardial infarction, (c) history of congestive heart failure, (d) history of cerebrovascular disease, (e) current treatment with insulin and (f) elevated serum creatine levels (e.g., ≥2.0 ng/mL). A score of three or greater constitutes the highest risk category.

The methods described herein are based on measuring and quantitating cell-derived microvesicles, generally referred to as extracellular vesicles (EVs). EVs are sub-micron vesicles that are produced by virtually every eukaryotic cell type, often in response to cellular activation, damage or death. EVs in circulation undergo rapid clearance by a variety of mechanisms; thus, EV concentrations in circulation are tightly related to their rate of production. EVs carry surface markers from their parent cell and, as a result, an EVs upstream cellular compartment source can be identified. See, for example, Choi & Lee, 2016, "Illuminating the physiology of extracellular vesicles," Stem Cell Res. Ther., 7(1):55; and Colombo et al., 2014, "Biogenesis, secretion, and intercellular interactions of exosomes and other extracellular vesicles," Annu. Rev. Cell Dev. Biol., 30:255-89.

EVs can be measured and quantitated using any number of technological approaches such as, without limitation, nanoparticle tracking, dynamic light scattering, or flow cytometry. Nanoparticle tracking and dynamic light scattering both have the advantage of being able to characterize the size distribution of EVs. In addition, nanoparticle tracking is able to measure particle concentrations and, in some configurations, is able to detect a single fluorescent label. Of the available technologies, only flow cytometry is able to detect multiple different surface markers simultaneously on individual vesicles. Due to their very small size, however, EVs are at the limit of detection via flow cytometry. Consequently, specialized methods of sample preparation and instrument operation (e.g., high-sensitivity flow cytometry) are required in order to reliably measure and quantify EVs using flow cytometry.

For methods related to obtaining and characterizing EVs, see, for example, Rupert et al., 2017, "Methods for the physical characterization and quantification of extracellular vesicles in biological samples," Biochim Biophys. Acta, 1861(1 Pt A):3164-79; Szatanek et al., 2017, "The Methods of Choice for Extracellular Vesicles (EVs) Characterization," Int. J. Mol. Sci., 18(6):1153; Coumans et al., 2017, "Methodological Guidelines to Study Extracellular Vesicles," Circ. Res., 120(10):1632-48; Gholizadeh et al., 2017, "Microfluidic approaches for isolation, detection, and characterization of extracellular vesicles: Current status and future directions," Biosens. Bioelectron., 91:588-605; Pugholm et al., 2015, "Antibody-based assays for phenotyping of extracellular vesicles," Biomed. Res. Int., 524817; Kreimer et al., 2015, "Mass-spectrometry-based molecular characterization of extracellular vesicles: lipidomics and proteomics," J. Proteome Res., 14(6):2367-84; Szatanek et al., 2015, "Isolation of extracellular vesicles: Determining the correct approach (Review)," Int. J. Mol. Med., 36(1): 11-7; and Pocsfalvi et al., 2016, "Mass spectrometry of extracellular vesicles," Mass Spectrom. Rev., 35(1):3-21.

As discussed herein, the EVs in the biological sample that are predictive of an individual who will experience a cardiovascular event following a surgical procedure (i.e., a non-cardiac surgical procedure) express a set of biological markers that includes at least one of CD31+, CD105+ or CD64+(e.g., at least two of CD31+, CD105+ or CD64+; all three of CD31+, CD105+ or CD64+). Also as discussed herein, the sensitivity and specificity of the predictive methods described herein increase with the use of additional markers. Those additional markers include CD41a–, CD47–, or combinations thereof.

Antibodies against any of these cell surface biological markers can be obtained from any number of commercial providers (e.g., BD Biosciences; R&D Systems; Signalway Antibody; Invitrogen Antibodies). Alternatively, antibodies against any of these cell surface biological markers can be produced using methods known in the art. Similarly, detectable labels for distinguishing between the different cell surface biological markers are known in the art (e.g., Alexa Fluor 405, 488, 700 or 750; Cy5, Cy5.5, or Cy7; eFluor 450, 605, 625 or 650; APC; GFP; FITC; DyLight 488, PE, PI, or combinations thereof), and many commercially-available antibodies can be obtained already labeled.

In the methods described herein, the number of EVs is determined in a biological sample from the individual. Typically, the biological sample is blood (e.g., platelet-poor plasma (PPP)). It would be appreciated that the risk analysis can be performed during a pre-surgical evaluation (e.g., at a doctor's office, e.g., a week or two before the non-cardiac surgical procedure is to take place), or the risk analysis can be performed immediately before the non-cardiac surgical procedure takes place (e.g., at a hospital or surgical center; e.g., hours or minutes before the non-cardiac surgical procedure is to take place).

The number of EVs in a biological sample that express the desired set of biological markers can be compared to a pre-determined value obtained, for example, by retrospective analysis of surgical patients who did not experience a cardiovascular event within 30 days after their surgical procedure. Based on the number of EVs in the individual's biological sample, the individual can be classified into a low-risk group (i.e., when the number of EVs in the biological sample that express the desired set of biological markers is equal to or less than the pre-determined value) or a high-risk group (i.e., when the number of EVs in the biological sample that express the desired set of biological markers is greater than the pre-determined value).

It would be appreciated that the pre-determined value will depend upon the particular methods used to obtain and determine the number of EVs in a biological sample as well as the sensitivity of the instrumentation used. Applying the particular methods and instrumentation described in the Example section below, the pre-determined value is about 10 EVs or less per microliter (mL) of plasma. For example, applying the methods and instrumentation used herein, a level of EVs of from about 0 to about 10 EVs per mL of plasma would be considered low risk.

In some instances, it may be desirable to consider both the risk prediction described herein (i.e., based on the number of EVs that express the desired set of biological markers) as well as the Revised Cardiac Risk Index (RCRI) for the individual when classifying the individual. For example, the classification of an individual can be based on a combination of the number of EVs in the biological sample with the various RCRI risk factors. The RCRI is the current standard-of-care method for assessing the risk of an individual for a post-surgical cardiovascular event, and the criteria for RCRI are described herein.

Based on the risk classification of the individual, the physician and the patient can determine whether or not to proceed with the non-cardiac surgical procedure. In instances in which the physician and the patient decide to delay the non-cardiac surgical procedure, they can attempt to improve the risk profile of the individual through medical treatment, lifestyle intervention, etc. In some instances, it may be desirable to monitor the individual over time and, if the risk profile fluctuates, the non-cardiac surgical procedure can be performed during an interval of lower risk.

The methods described herein also can be used to detect the presence of vulnerable plaques in an individual based on the number of monocyte-derived extracellular vesicles (MEVs). As described herein, an increase in the number of MEVs in the biological sample is an indication of plaque vulnerability in the individual. In some instances, it may be desirable to consider both the presence of vulnerable plaques as described herein (i.e., based on the number of MEVs that express the desired set of biological markers) as well as other laboratory tests like cholesterol, or other imaging tests such as calcium score when classifying the individual.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Preliminary Experiments and Results

Analytical procedures for measuring and quantifying EVs via flow cytometry have developed and been refined, with up to nine distinct fluorescently-labeled cell surface markers. Using these procedures, it was first demonstrated that EVs, together with certain cells with angiogenic potential, were differentially expressed in people with poor endothelial health (i.e. patients with type 2 diabetes mellitus or atherosclerosis) compared with apparently healthy controls (Kurtzman et al., 2013, Cytom. B Clin. Cytom., 84:255-66). In a small follow-up study, it was subsequently shown that this combined cell- and EV-derived "Vascular Health Profile" predicted the future development of adverse cardiovascular events, including myocardial infarction, major adverse cardiovascular event (MACE) and stroke (Rogers et al., 2015, Cytom. B Clin. Cytom., doi: 10.1002/cyto.b.21337).

Example 2—Clinical Trial Inclusion

Based on the preliminary findings described in Example 1, a clinical trial was conducted for patients undergoing non-cardiac vascular surgery. The primary aim of the trial was to determine if cell and EV profiling via specialized flow cytometry, performed just prior to surgery, is able to predict the occurrence of cardiovascular events within 30 days after surgery. Inclusion criteria included major vascular surgeries such as carotid endarterectomy, abdominal aortic aneurysm repair, repair of abdominal occlusive disease, axillary-femoral bypass, femoral endarterectomy, and lower extremity bypass. Cardiac procedures (e.g. cardiac artery bypass) were excluded. Emergent procedures were excluded due to difficulty of obtaining informed consent. The included procedures are all classified as high-risk vascular surgical procedures. Cardiovascular events were adjudicated by an independent panel of physicians, and included myocardial infarction, emergency cardiac revascularization, death (collectively, MACE), or myocardial injury following non-cardiac surgery (MINS).

Example 3—Sample Preparation and Flow Cytometry

Blood was drawn in sodium citrate tubes (blue top), using a 21-gauge needle and 7-inch butterfly tubing. Within 6 hours of the blood draw, platelet-poor plasma (PPP) was prepared in a two-step centrifugation protocol. In the first step, the blood was centrifuged at 2500×g for 15 minutes with low brake, collecting the plasma using a measuring gauge above the buffy coat. In the second step, the collected plasma was centrifuged at 2500×g for 15 minutes with low brake, and PPP was collected, leaving 0.5 mL behind.

PPP was prepared for high-sensitivity flow cytometric analysis by staining 50 µL of PPP in a Trucount tube with an antibody panel comprised as follows: (a) V500-Annexin V (BD, Cat #561501); (b) V450-CD144 (BD, Cat #561569, clone 55-7H1); (c) PE-Cy7-CD31 (BD, Cat #563651, clone WM59); (d) APC R700-CD64 (BD, Cat #657701, clone MD22); (e) AF647-CD105 (BD, Cat #561439, clone 266); (f) APC-H7-CD41a (BD, Cat #561422, clone HIPS); (g) PerCP-Cy5.5-CD3 (BD, Cat #340948, clone SK7); and (h) PE-CD47 (BD, Cat #556046, clone B6H12).

Samples were incubated in the dark for 20-30 min and analyzed immediately on the flow cytometer. The flow cytometer instrument used was a specially modified version of the Becton Dickinson FACSCantoPlus flow cytometer. Modifications were designed to increase the small particle sensitivity of the instrument, and included (a) modifications to the Side Scatter detector to limit the field of view and thus, limit background signal, and (b) increasing the blue laser intensity from the standard 20 mW to 200 mW. The instrument was triggered on the Side Scatter signal, and Window Extension was set to a minimal value (0.2) to limit background variance.

Example 4—Data Acquisition and Analysis

Prior to sample data acquisition each day, the instrument was standardized to a stable bead reference material (CS&T, Becton Dickinson) to reproduce fluorescence sensitivity for each of the eight fluorescence detectors. Size reference standards (platelet-rich plasma stained with CD41a APC-H7 and 200 nm silica beads) were used to reproducibly set an upper size cutoff of approximately 1.0 μm. Finally, an EV negative control sample was created by tritonizing the sample after acquisition of primary data, and then running it again. TRITON™ was used to disrupt the bi-lipid membrane of EVs, but otherwise leave the stained PPP sample unchanged. The resulting signals were used to compute positivity thresholds for each of the eight fluorescence detectors.

"Events" in the flow cytometry data file were defined as particles passing through the instrument that generated a Side Scatter signal large enough to trigger signal acquisition. The expression values of each of the eight markers in the panel were determined for each event to be either "positive" or "negative" by comparison for each event of the intensity of each marker with the positivity thresholds determined from the tritonized negative control sample. Great care was taken to operate at sample concentrations that precluded the chance occurrence of multiple EVs coincidentally present in the detection volume ("poisson coincidence").

Analysis of the data was performed using computational data analysis algorithms based on the R computer language (R_Development_Core_Team, R: A language and environment for statistical computing. Vienna, Austria, R Foundation for Statistical Computing, 2008) and Bioconductor (Gentleman et al., 2004, Genome Biol., 5:R80) methods customized specifically for the analysis of the data in this study. Computational gating was used instead of manually setting thresholds by visual inspection of EV distributions, which is the current standard method of analysis of flow cytometry data, in order to provide a more quantitative, less subjective determination of EV subsets, as well as to enable the exhaustive determination of all possible combinations of the markers present in the panel.

Flow cytometry events were defined to be EVs if and only if (a) the event was below the size cutoff value on the Side Scatter signal, and (b) if the event had positive expression for at least one of the eight surface markers in the panel. All non-EV events were presumed to be non-vesicular matter (confirmed by the tritonized negative control sample), and excluded from further consideration. EV counts were placed on an absolute scale by normalizing raw counts to the Trucount beads, enabling the expression of each EV subset as number of EVs per unit volume of plasma.

Example 5—Subjects and Statistical Analysis

Altogether, 225 patients were recruited consecutively from 4 institutions. Of these, pre-surgical blood samples were successfully obtained and analyzed (i.e., within 48 hours prior to surgery) for 217 subjects. Of the 217 subjects for whom preoperative data were obtained, 19 experienced a cardiovascular event, as defined above.

A correspondence between EV phenotypic subsets, measured before surgery, and the occurrence of a post-surgical cardiovascular event within 30 days after surgery was examined. To do this, all binary (either positive or negative) combinations of expression of the seven markers in the panel, which indicate the parent cell of the EV, were enumerated (note that Annexin V does not indicate the origin of the cell, but rather the mechanism of EV production, and so was excluded here). This gives rise to $2^7$ (=128) possible EV subsets. Study subjects were divided into (a) the group that experienced a cardiovascular event (n=19) and (b) the group that did not experience an event (n=198). Univariate statistics were then calculated, using the rank-sum Mann-Whitney test, of the probability (P-value) that the concentration of each EV subset was drawn from the same parent population for the two groups of patients. A low P-value indicates that the two groups have a high likelihood of differing with respect to this EV measure. Finally, because multiple (i.e., 128) hypotheses were tested, the P-values were corrected using the Bonferroni correction to control for false discovery.

Example 6—Identification of a Phenotype Associated with Cardiovascular Events after Surgery Using the procedure described herein, it was found that only one of the 128 enumerated EV subsets differed significantly between the two groups of patients. This subset is characterized by positive expression of CD31, CD105 and CD64, and negative expression of CD47, CD3, CD41a and CD144. The Bonferroni-corrected P-value for this subset was 0.002, while the un-adjusted P-value was $1.87 \times 10^{-5}$. FIG. 1 shows a boxplot comparing the concentration of EVs of this phenotype in the two groups of patients. No other subsets showed a statistically-significant difference between the two groups when corrected for multiple comparisons.

A sensitivity analysis was undertaken to determine which subgroup of the seven marker specificities carried the most significance in defining the informative subset of EVs. This analysis revealed that omitting either or both of the CD3 or the CD144 specificities resulted in a minimal change in P-value, from $1.87 \times 10^{-5}$ to $2.0 \times 10^{-5}$. Omitting the CD41 a$^-$ specificity resulted in a P-value increase to $2.8 \times 10^{-4}$, and omission of the CD47$^-$ specificity resulted in an increase to $1.5 \times 10^{-3}$. Omission of any of the three positively expressed specificities of CD31$^+$, CD105$^+$ or CD64$^+$ resulted in a substantial loss of statistical significance, with CD31$^+$ being the most influential of the three, and CD64$^+$ being the least.

The sensitivity of the target EV subset to its constituent markers was further explored using the Bioconductor package RchyOptimyx (Adrin Jalali A, Aghaeepour N, Rchyoptimyx: Optimyzed cellular hierarchies for flow cytometry. 2012). RchyOptimyx models all possible gating strategies that can be generated within a specific panel, and uses dynamic programing and optimization tools from graph-theory to determine the minimal sets of markers that can identify a target population to a desired level of statistical significance with respect to a dependent variable (in this case, the occurrence of a cardiovascular event after surgery). A hierarchy of EV phenotypes was constructed as a directed acyclic graph (DAG), with one node on the top-most level representing all EVs, and nodes further down showing successively more specific EV populations. Intermediate populations were placed in the hierarchy using parent-child relationships based on their evolution of statistical significance. Annexin V was included in this analysis as well as the cell-identifying markers in order to assess the global phenotypic sensitivity. Notably, neither CD3 nor Annexin V appear in any node of the tree depicted in FIG.

2, indicating that neither of these markers contributed to the development of statistical significance of the target phenotype. This analysis also demonstrated that, while the three positively-expressed markers (CD31, CD105 and CD64) are required to define the informative phenotype, the addition of negative expression of CD47 and CD41a, either alone or together, substantially improves the specificity of the subset. Finally, the addition of CD144$^-$ had a negligible impact on the overall P-value.

Thus, we concluded that the defining core informative phenotype is CD31$^+$/CD 105$^+$/CD64$^+$. Adding a negative gate for CD47 and/or CD41 a significantly increased the specificity of the EV phenotype for the prediction of cardiovascular event after non-cardiac vascular surgery. Specifying expression of CD3, CD144 and Annexin V only marginally influenced the predictive power of the EV subset.

The only known cell type to express all three of the defining markers (CD31, CD105 and CD64) of the EV subset related to the occurrence of a post-surgical event are monocytes/macrophages. It is well known that these cells play an important role in the development of atherosclerotic plaque as well as in the transition of plaque status from stable to unstable/vulnerable (Narula et al., 2013, J. Am. Coll. Cardiol., 61:1041-51; Virmani et al., 2006, J. Am. Coll. Cardiol., 47:C13-8), and finally to rupture (Shah, 2003, J. Am. Coll. Cardiol., 41:15S-22S). It has also been shown that atherosclerotic plaques contain large numbers of EVs, and their composition is markedly different from EVs in circulation (Leroyer et al., 2007, J. Am. Coll. Cardiol., 49:772-77). Thus, one interpretation of these findings is that unstable plaque represents a prolific source of monocyte-, macrophage-, or foam cell-derived EVs (collectively, MEVs). It was hypothesized that MEVs are a potent biomarker for plaque vulnerability, and that in patients destined to experience a post-surgical cardiovascular event, these MEVs are present at significantly higher concentrations compared to patients who do not go on to experience a cardiovascular event.

Example 7—Validation of Predictive Methods

Figure 3:
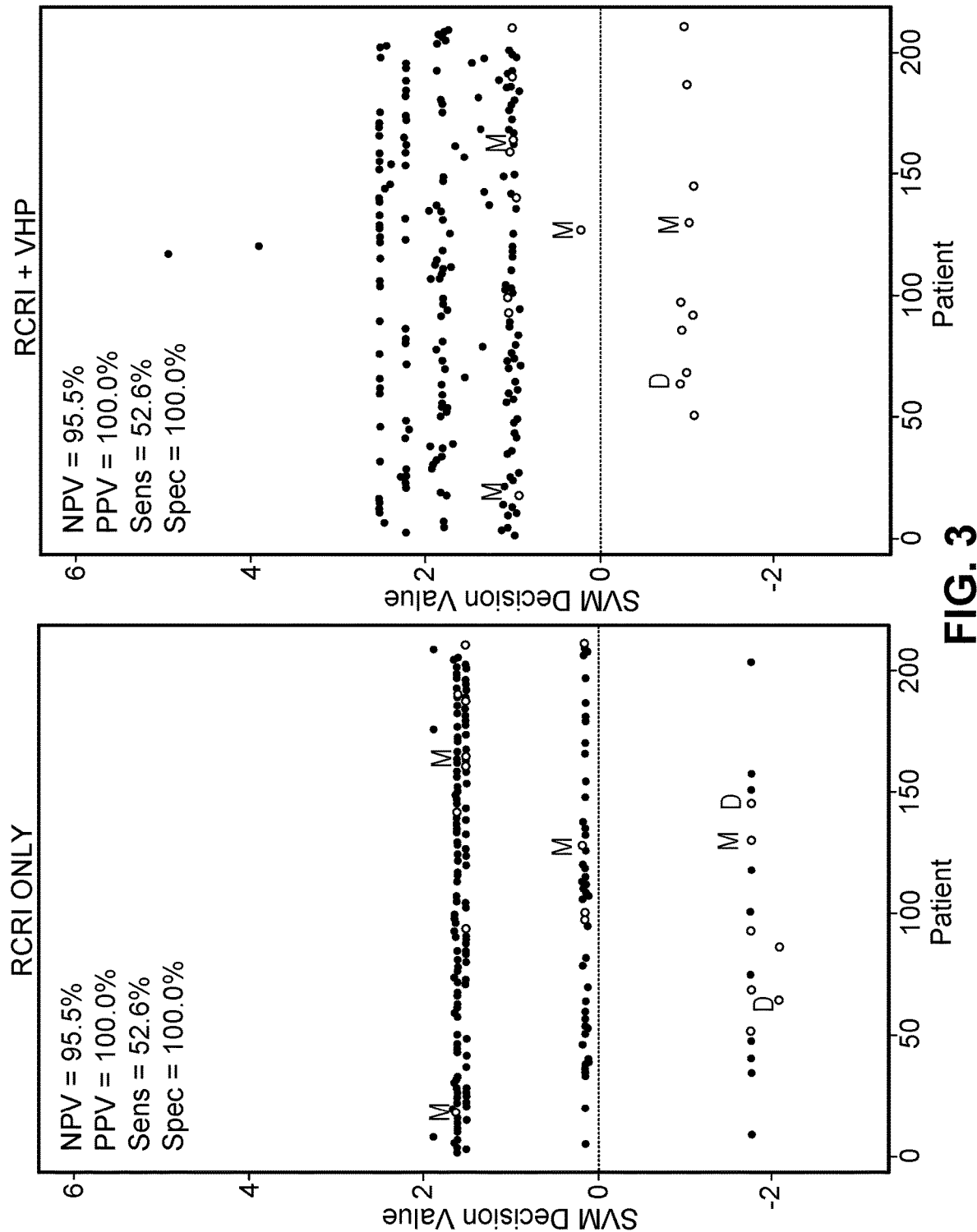
FIG. 3 is experimental data showing the cross-validated support vector machine classifiers. The left panel shows an SVM using only categorical features included in the RCRI. The right panel shows the addition of the EV informative measure. Points are individual subjects (red=Event, blue=No Event). Points below zero are classified as "Event", while points above zero are classified as "No Event". "D" marks subjects who died; "M" marks subjects who experienced myocardial infarction.

While FIG. 1 indicates that the EV enumeration alone is a powerful measure of the risk of a patient for a post-surgical cardiovascular event, machine learning techniques were then employed in a multivariate setting to further estimate the accuracy with which it is possible to predict which patients are likely to experience a post-surgical cardiovascular event. The method of Support Vector Machine (SVM) was used to build classifiers. Since the sample size is relatively small (19 events out of a total of 217 subjects), k-fold cross validation (k=2, 5, 10) as well as leave-one-out cross validation was used to control for over-fitting the predictive classifiers. The results of the various cross-validation schemes were substantially equivalent. FIG. 3 shows the resulting cross-validated SVM classifiers. This figure indicates that the addition of the EV measurement to the features comprising the Revised Cardiac Risk Index (RCRI) increases the accuracy of predicting the future post-surgical occurrence of a cardiovascular event. Both the sensitivity and specificity of the prediction improve with the addition of the EV measurement, however, the improvement in specificity is dramatic, from 94.6% to 100%. This increase in specificity drives the increase in positive predictive value (PPV) from 41.2% to 100%.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of classifying risk of having a cardiovascular event after a non-cardiac vascular surgical procedure in an individual, the method comprising
providing a biological sample from the individual;
via flow cytometry, determining the number of extracellular vesicles (EVs) in the biological sample expressing a set of biological markers, the set of biological markers comprising at least two of CD31+, CD105+, and CD64+; and
classifying the individual as low risk of having a post-surgical cardiovascular event or as high risk of having a post-surgical cardiovascular event based upon the number of EVs in the biological sample expressing the set of biological markers.

2. The method of claim 1, wherein the cardiovascular event is selected from the group consisting of myocardial infarction, emergency cardiac revascularization, stroke, death, and myocardial injury following non-cardiac surgery (MINS).

3. The method of claim 1, wherein the biological sample is blood.

4. The method of claim 1, wherein the set of biological markers comprises CD31+ and CD105+.

5. The method of claim 1, wherein the set of biological markers comprises CD31+ and CD64+.

6. The method of claim 1, wherein the set of biological markers comprises CD31+, CD105+ and CD64+.

7. The method of claim 1, wherein the set of biological markers further comprising CD41a–.

8. The method of claim 1, wherein the set of biological markers further comprising CD47–.

9. The method of claim 1, wherein the set of biological markers comprises CD31+, CD105+, CD64+, CD41a– and CD47–.

10. The method of claim 1, further comprising preparing platelet-poor plasma (PPP) from the biological sample prior to determining the number of EVs.

11. The method of claim 1, further comprising comparing the number of EVs in the biological sample expressing the set of biological markers to a pre-determined value, wherein the individual is classified into the low-risk group when the number of EVs in the biological sample expressing the set of biological markers is less than the pre-determined value and wherein the individual is classified into the high-risk group when the number of EVs in the biological sample expressing the set of biological markers is greater than the pre-determined value.

12. The method of claim 1, further comprising determining the Revised Cardiac Risk Index (RCRI) for the individual.

13. The method of claim 12, wherein the RCRI is determined using risk factors selected from the group consisting of history of myocardial infarction, history of congestive heart failure, history of cerebrovascular disease, insulin use, and a serum creatine level of ≥2.0 ng/mL.

14. The method of claim 12, wherein the classifying step is further based on combining the RCRI with the number of EVs in the biological sample.

15. A method of detecting the presence of vulnerable plaques in an individual, comprising:
   providing a biological sample from the individual; and
   via flow cytometry, determining the number of monocyte-derived extracellular vesicles (MEVs) in the biological sample expressing a set of biological markers, the set of biological markers comprising at least two of CD31+, CD105+, and/or CD64+;
   wherein an increase in the number of MEVs in the biological sample is indicative of plaque vulnerability.

* * * * *